United States Patent
Sussman et al.

[11] Patent Number: 6,110,162
[45] Date of Patent: Aug. 29, 2000

[54] LIQUEFACTION HANDPIECE

[75] Inventors: Glenn Sussman, Lake Forest, Calif.;
Thomas G. Capetan, Fort Worth, Tex.;
Donald M. Cohen, Irvine, Calif.

[73] Assignee: Alcon Laboratories, Inc.

[21] Appl. No.: 09/374,854

[22] Filed: Aug. 16, 1999

Related U.S. Application Data

[63] Continuation of application No. 09/090,433, Jun. 4, 1998.
[51] Int. Cl.$^7$ .................................................. A61M 31/00
[52] U.S. Cl. .............................. 604/521; 604/22; 606/107
[58] Field of Search ................................. 604/19, 22, 27, 604/28, 30, 35, 48, 500, 521; 606/6, 107, 128

[56] References Cited

U.S. PATENT DOCUMENTS

| | | |
|---|---|---|
| 1,493,450 | 5/1924 | Richardson . |
| 3,589,363 | 6/1971 | Banko et al. . |
| 3,818,913 | 6/1974 | Wallach . |
| 3,930,505 | 1/1976 | Wallach . |
| 4,024,866 | 5/1977 | Wallach . |
| 4,223,676 | 9/1980 | Wuchinich . |
| 4,246,902 | 1/1981 | Martinez . |
| 4,249,899 | 2/1981 | Davis . |
| 4,265,618 | 5/1981 | Herskovitz et al. . |
| 4,301,802 | 11/1981 | Poler . |
| 4,517,977 | 5/1985 | Frost . |
| 4,570,632 | 2/1986 | Woods . |
| 4,577,629 | 3/1986 | Martinez . |
| 4,589,415 | 5/1986 | Haaga . |
| 4,609,368 | 9/1986 | Dotson, Jr. . |
| 4,662,869 | 5/1987 | Wright . |
| 4,674,502 | 6/1987 | Imonti . |
| 4,696,298 | 9/1987 | Higgins et al. . |
| 4,911,161 | 3/1990 | Schechter . |
| 4,922,902 | 5/1990 | Wuchinich et al. . |
| 5,226,910 | 7/1993 | Kajiyama et al. . |
| 5,250,065 | 10/1993 | Clement et al. . |
| 5,261,883 | 11/1993 | Hood et al. . |
| 5,275,607 | 1/1994 | Lo et al. . |
| 5,285,795 | 2/1994 | Ryan et al. . |
| 5,322,504 | 6/1994 | Doherty et al. . |
| 5,423,330 | 6/1995 | Lee . |
| 5,554,155 | 9/1996 | Awh et al. . |
| 5,562,692 | 10/1996 | Bair . |
| 5,591,184 | 1/1997 | McDonnell . |
| 5,616,120 | 4/1997 | Andrew . |
| 5,624,392 | 4/1997 | Saab . |
| 5,624,393 | 4/1997 | Diamond . |
| 5,653,692 | 8/1997 | Masterson et al. . |
| 5,674,226 | 10/1997 | Doherty et al. . |
| 5,766,194 | 6/1998 | Smith . |
| 5,865,790 | 2/1999 | Bair . |
| 5,879,347 | 3/1999 | Saadat . |
| 5,891,095 | 4/1999 | Eggers et al. . |
| 5,947,988 | 9/1999 | Smith . |

FOREIGN PATENT DOCUMENTS

WO 96/24314   8/1996   WIPO .

*Primary Examiner*—Wynn Wood Coggins
*Assistant Examiner*—Deborah Blyveis
*Attorney, Agent, or Firm*—Jeffrey S. Schira

[57] ABSTRACT

A surgical handpiece having at least two lumens mounted to a body. At least one lumen is used for aspiration and at least one other lumen is used to inject heated surgical fluid for liquefying a cataractous lens. A portion of the second lumen is enlarged to form a pumping chamber. The pumping chamber works by boiling a small volume of the surgical fluid. As the fluid boils, it expands rapidly, thereby propelling the liquid downstream of the pumping chamber out of the second lumen. The pumping chamber may use any type of heater, such as a resistive heater or an induction heater. The handpiece may also contain other lumens for injecting relatively cool surgical fluid.

4 Claims, 7 Drawing Sheets

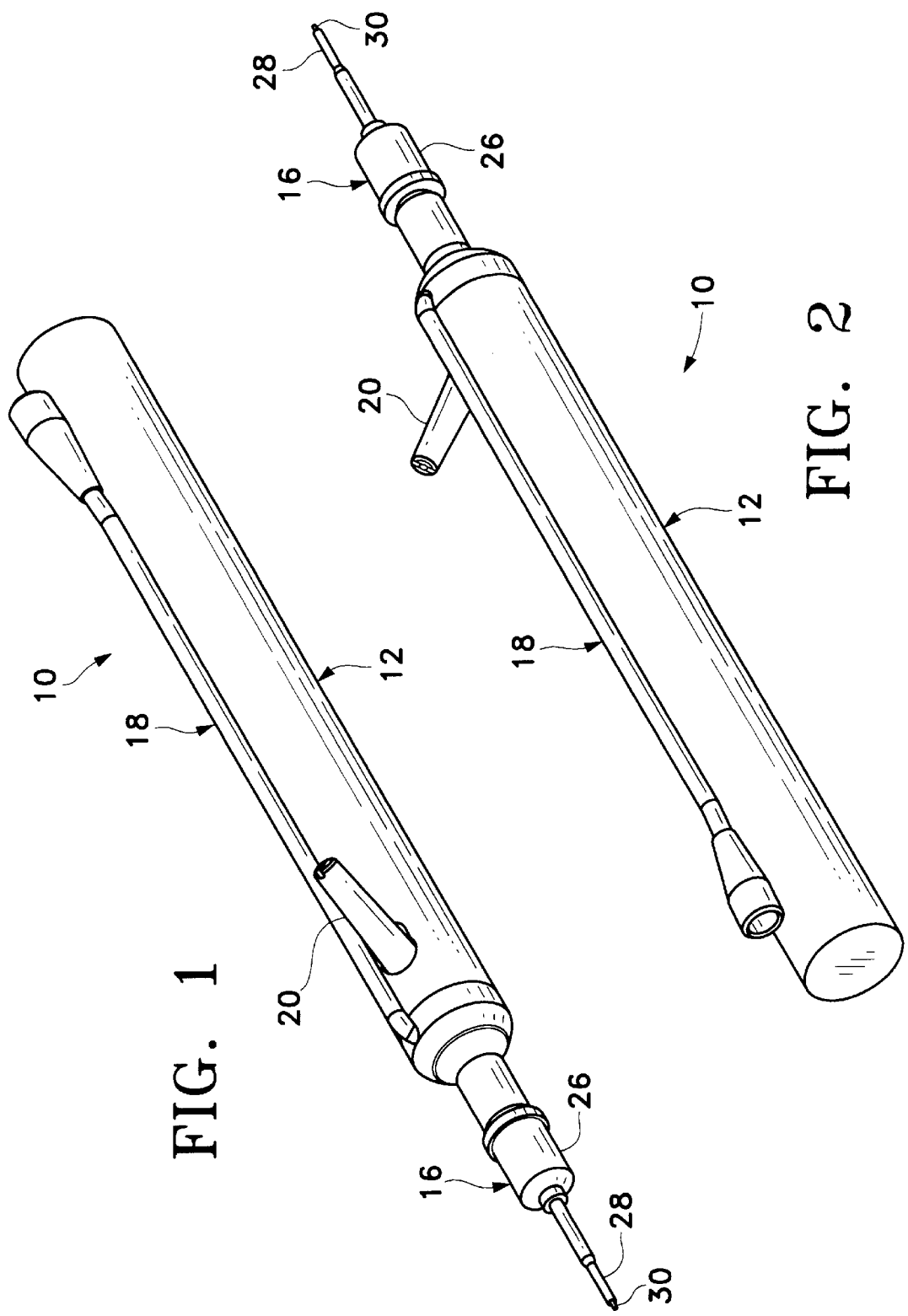

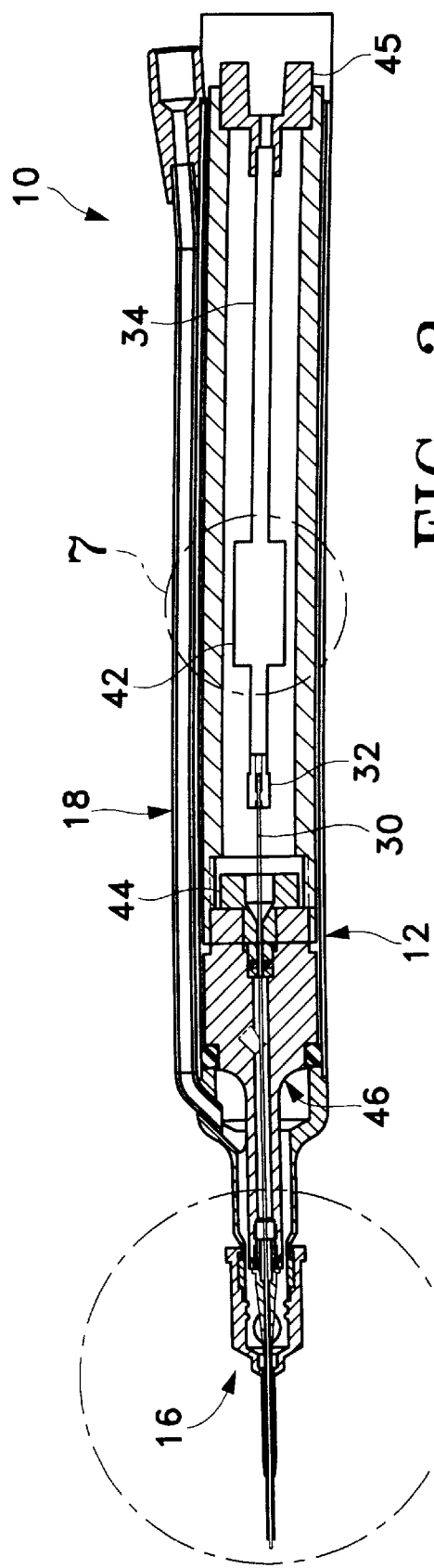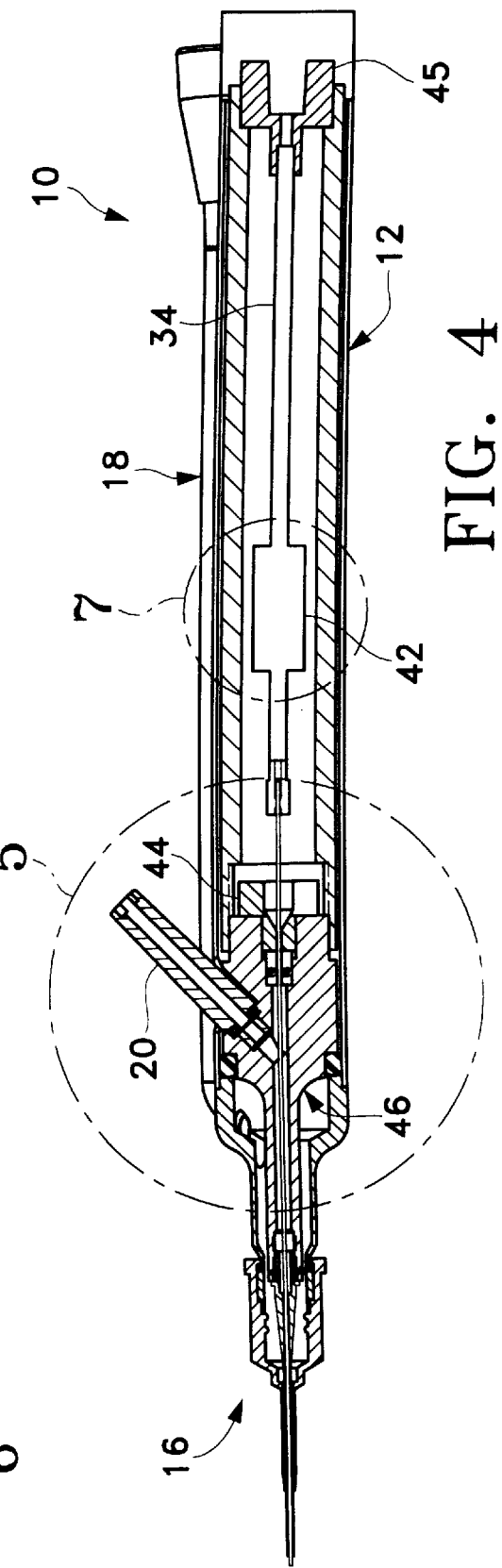

LIQUEFACTION HANDPIECE

This application is a continuation of U.S. patent application Ser. No. 09/090,433, filed Jun. 4, 1998.

BACKGROUND OF THE INVENTION

This invention relates generally to the field of cataract surgery and more particularly to a handpiece for practicing the liquefaction technique of cataract removal.

The human eye in its simplest term functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease caused the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In this United States, the majority of cataractous lenses are removed by a surgical technique called phacoemulsification. During this procedures, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat Nos. 3,589,363; 4,223,676; 4,246,902; 4,493,694; 4,515,583; 4,589,415; 4,609,368; 4,869,715; 4,922,902; 4,989,583; 5,151,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

Recently, a new cataract removal technique has been developed that involves the injection of hot (approximately 45° C. to 105° C.) water or saline to liquefy or gellate the hard lens nucleus, thereby making it possible to aspirate the liquefied lens from the eye. Aspiration is conducted with the injection of the heated solution and the injection of a relatively cool solution, thereby quickly cooling and removing the heated solution. This technique is more fully described in U.S. Pat. No. 5,616,120 (Andrew, et al.), the entire contents of which is incorporated herein by reference. The apparatus disclosed in the publication, however, heats the solution separately from the surgical handpiece. Temperature control of the heated solution can be difficult because the fluid tubings feeding the handpiece typically are up to two meters long, and the heated solution can cool considerably as it travels down the length of the tubing.

Therefore, a need continues to exist for a surgical handpiece that can heat internally the solution used to perform the liquefaction technique.

BRIEF SUMMARY OF THE INVENTION

The present invention improves upon the prior art by proving a surgical handpiece having at least two lumens mounted to a body. At least one lumen is used for aspiration and at least one other lumen is used to inject heated surgical fluid for liquefying a cataractous lens. A portion of the second lumen is enlarged to form a pumping chamber. The pumping chamber works by boiling a small volume of the surgical fluid. As the fluid boils, it expands rapidly, thereby propelling the liquid downstream of the pumping chamber out of the second lumen. The pumping chamber may use any type of heater, such as a resistive heater or an induction heater. The handpiece may also contain other lumens for injection relatively cool surgical fluid.

Accordingly, one objective of the present invention is to provide a surgical handpiece having at least two lumens.

Another objective of the present invention is to provide a surgical handpiece having a pumping chamber.

Another objective of the present invention is to provide a surgical handpiece having a device for delivering the surgical fluid through the handpiece in pulses.

These and other advantages and objectives of the present invention will become apparent from the detailed description and claims that follows.

BRIEF DESCRIPTION OF THE DRAWINGS

FIG. 1 is a front, upper left perspective view of the handpiece of the present invention.

FIG. 2 is a rear, upper right perspective view of the handpiece of the present invention.

FIG. 3 is a cross-sectional view of the handpiece of the present invention taken along a plane passing through the irrigation channel.

FIG. 4 is a cross-sectional view of the handpiece of the present invention taken along a plan passing through the aspiration channel.

DETAILED DESCRIPTION OF THE INVENTION

Figure 6:
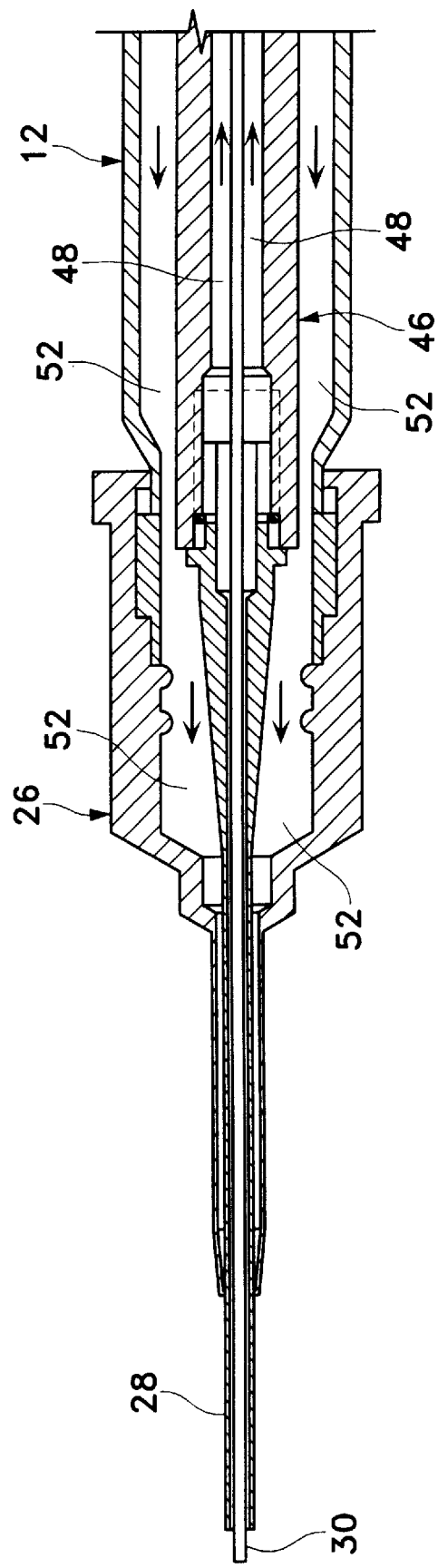
FIG. 6 is an enlarged partial cross-sectional view of the handpiece of the present invention taken at circle 6 in FIG. 3.

Handpiece 10 of the present invention generally includes handpiece body 12 and operative tip 16. Body 12 generally includes external irrigation lumen 18 and aspiration fitting 20. Body 12 is similar in construction to well-known in the art phacoemulsification handpieces and may be made from plastic, titanium or stainless steel. As best seen in FIG. 6, operative tip 16 includes tip/cap sleeve 26, needle 28 and lumen 30. Sleeve 26 may be any suitable commercially available phacoemulsification tip/cap sleeve or sleeve 26 may be incorporated into other tubes as a multi-lumen tube. Needle 28 may be any commercially available hollow phacoemulsification cutting tip, such as the TURBOSON-ICS tip available from Alcon Laboratories, Inc., Forth Worth, Tex. Lumen 30 may be any suitably sized tubing to fit within needle 28, for example 29 gauge hypodermic needle tubing.

Figure 5:
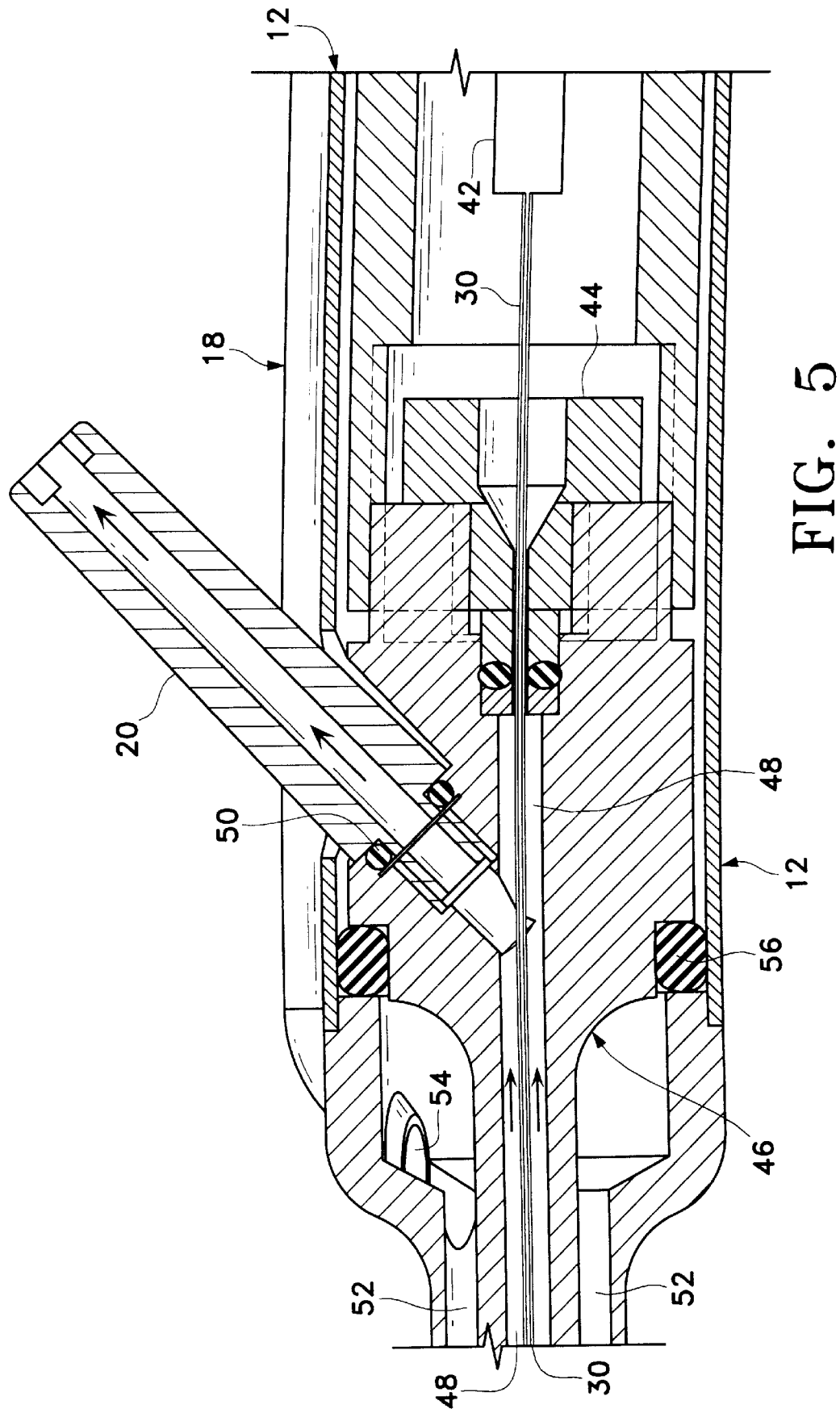
FIG. 5 is an enlarged partial cross-sectional view of the handpiece of the present invention taken at circle 5 in FIG. 4.

As best seen in FIG. 5, lumen 30 is free on the distal end and connected to pumping chamber 42 on the proximal end. Lumen 30 and pumping chamber 42 may be sealed fluid tight by any suitable means having a relatively high melting point, such as silver solder. Fitting 44 holds lumen 30 within bore 48 of aspiration horn 46. Bore 48 communicates with fitting 20, which is journaled into horn 46 and sealed with O-ring seal 50 to form an aspiration pathway through horn 46 and out fitting 20. Horn 46 is held within body 12 by O-ring seal 56 to form irrigation lumen 52 which communicates with irrigation lumen 18 at port 54.

Figure 7:
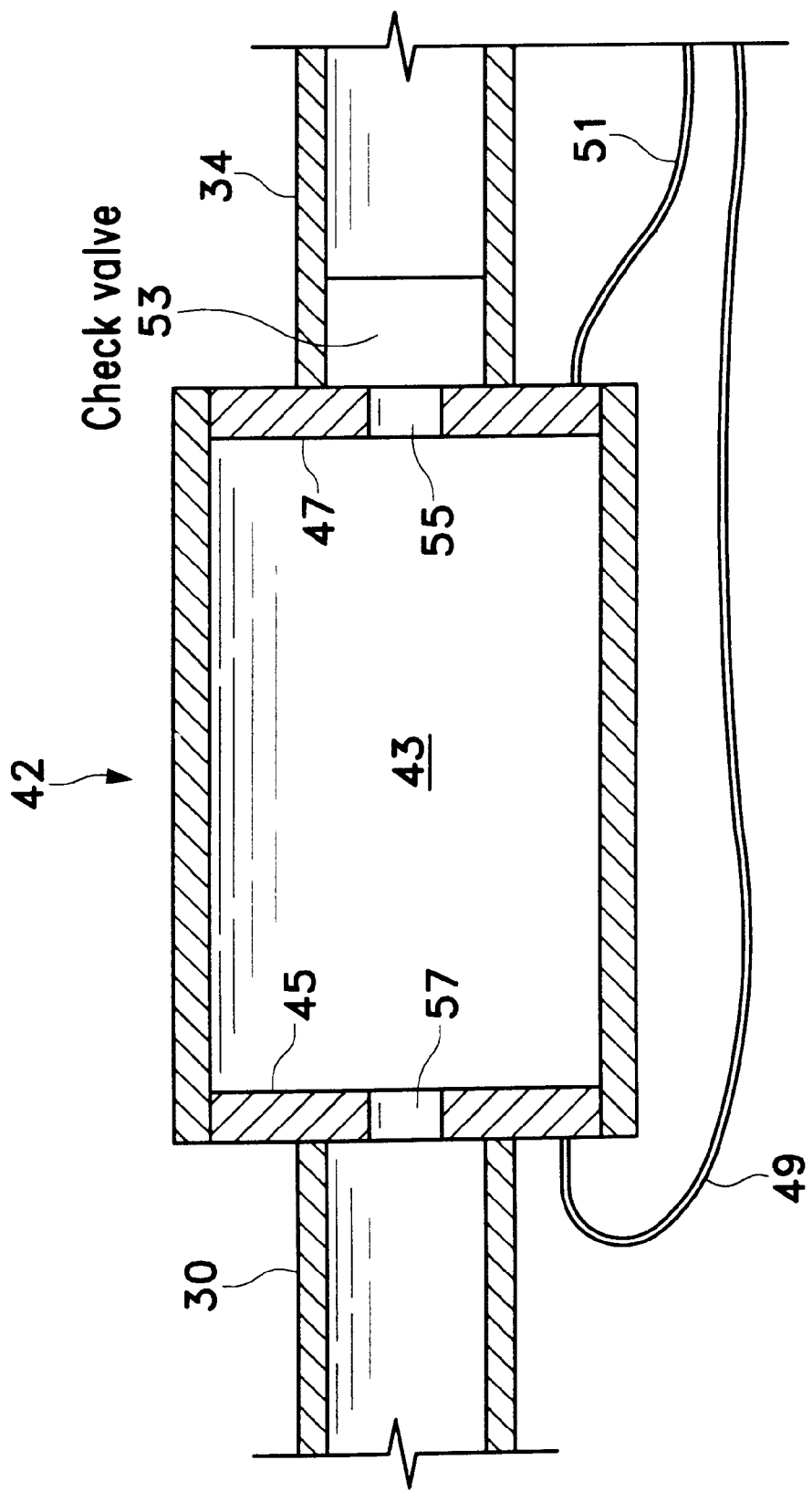
FIG. 7 is an enlarged cross-sectional view of the handpiece of the present invention taken at circle 7 in FIGS. 3 and 4, and showing a resistive boiler pump.

As best seen in FIG. 7, in a first embodiment of the present invention, pumping chamber 42 contains a relatively large pumping reservoir 43 that is sealed on both ends by electrodes 45 and 47. Electrical power is supplied to electrodes 45 and 47 by insulated wires 49 and 51, respectively, In use, surgical fluid (e.g. saline irrigating solution) enters reservoir 43 though port 55, lumen 34 and check valve 53 check valves 53 being well-known in the art. Electrical current (preferably Radio Frequency Alternating Current RFAC) is delivered to and across electrodes 45 and 47 because of the conductive nature of the surgical fluid. As the current flows though the surgical fluid, the surgical fluid boils. As the surgical fluid boils, it expands rapidly out of pumping chamber 42 through port 57 and into lumen 30 (check valve 53 prevents the expanding fluid from entering lumen 34). The expanding gas bubble pushes the surgical fluid in lumen 30 downstream of pumping chamber 42 forward. Subsequent pulses of electrical current form sequential gas bubbles that move surgical fluid down lumen 30. The size and pressure of the fluid pulse obtained by pumping chamber 42 can be varied by varying the length, timing and/or power of the electrical pulse sent to electrodes 45 and 47 and by varying the dimensions of reservoir 43. In addition, the surgical fluid may be preheated prior to entering pumping chamber 42. Preheating the surgical fluid will decrease the power required by pumping chamber 42 and/or increase the speed at which pressure pulses can be generated.

While several embodiments of the handpiece of the present invention are disclosed, any handpiece producing adequate pressure pulse force, rise time and frequency may also be used. For example, any suitable handpiece producing a pressure pulse force of between 0.03 grams and 3.0 grams, with a rise time of between 1 gram/sec. and 3,000 grams/sec and a frequency of between 1 Hz and 200 Hz may be used, with between 20 Hz and 100 Hz being most preferred. The pressure pulse force and frequency will vary with the hardness of the material being removed. For example, the inventors have found that a lower frequency with a higher pulse force is most efficient at debulking and removing the relatively hard nuclear material, with a higher frequency and lower pulse force being useful in removing softer epinuclear and cortical material. Infusion pressure, aspiration flow rate and vacuum limit and similar to current phacoemulsification techniques.

Figure 8:
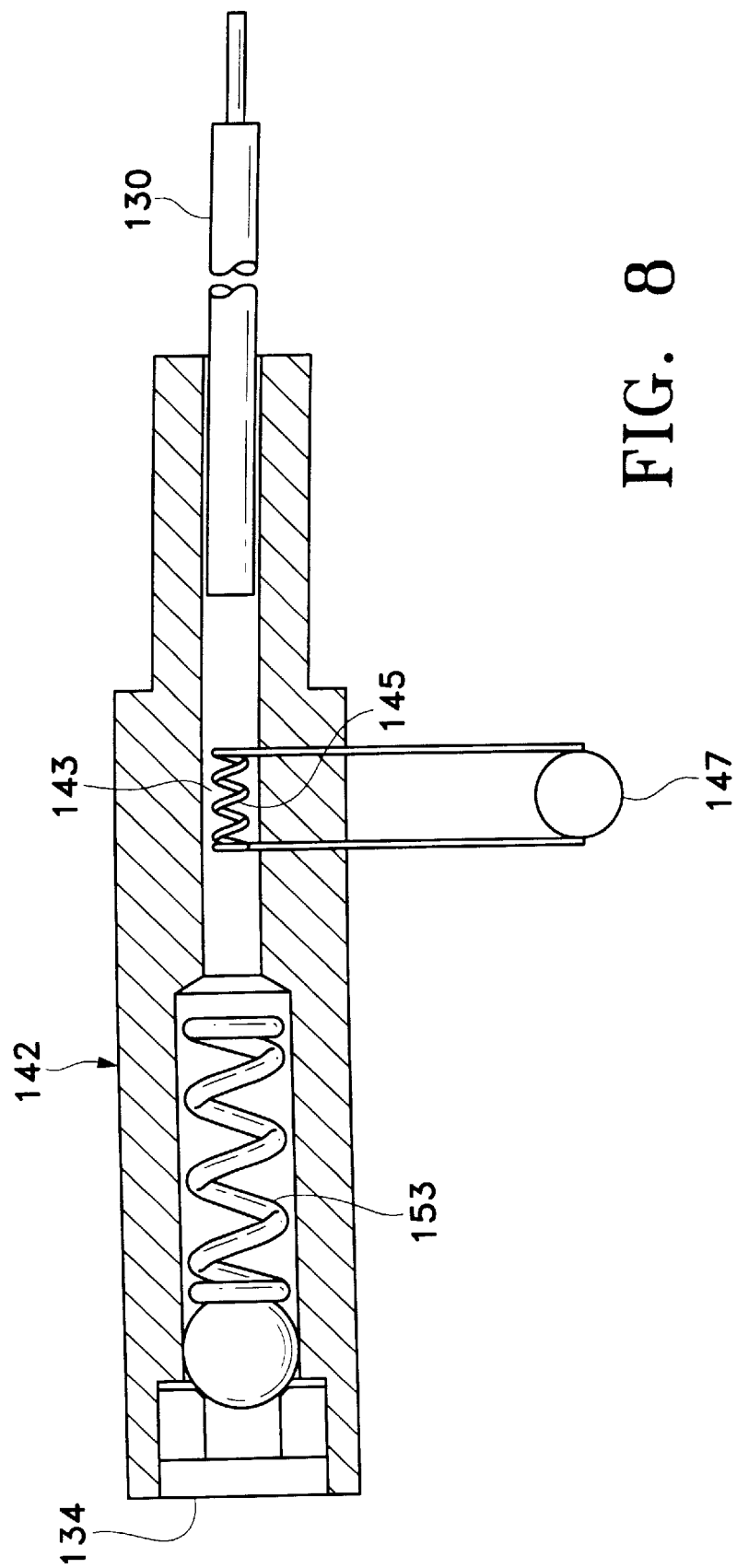
FIG. 8 is a schematic cross-sectional view of a heating element boiler pump that may be used with the present invention.

As best seen in FIG. 8, the fluid in reservoir 143 in pumping chamber 142 may also be heated by the use of heating element 145 that is internal to reservoir 143. Heating element 145 may be, for example, a coil of 0.003 inch diameter stainless steel wire which is energized by power source 147. The size and pressure of the fluid pulse obtained by pumping chamber 142 can be varied by varying the length and timing of the electrical pulse sent to element 145 by power source 147 and by varying the dimension of reservoir 143. The numbers in FIG. 8 are identical to the numbers in FIG. 7 except for the addition of "100" in FIG. 8.

Figure 9:
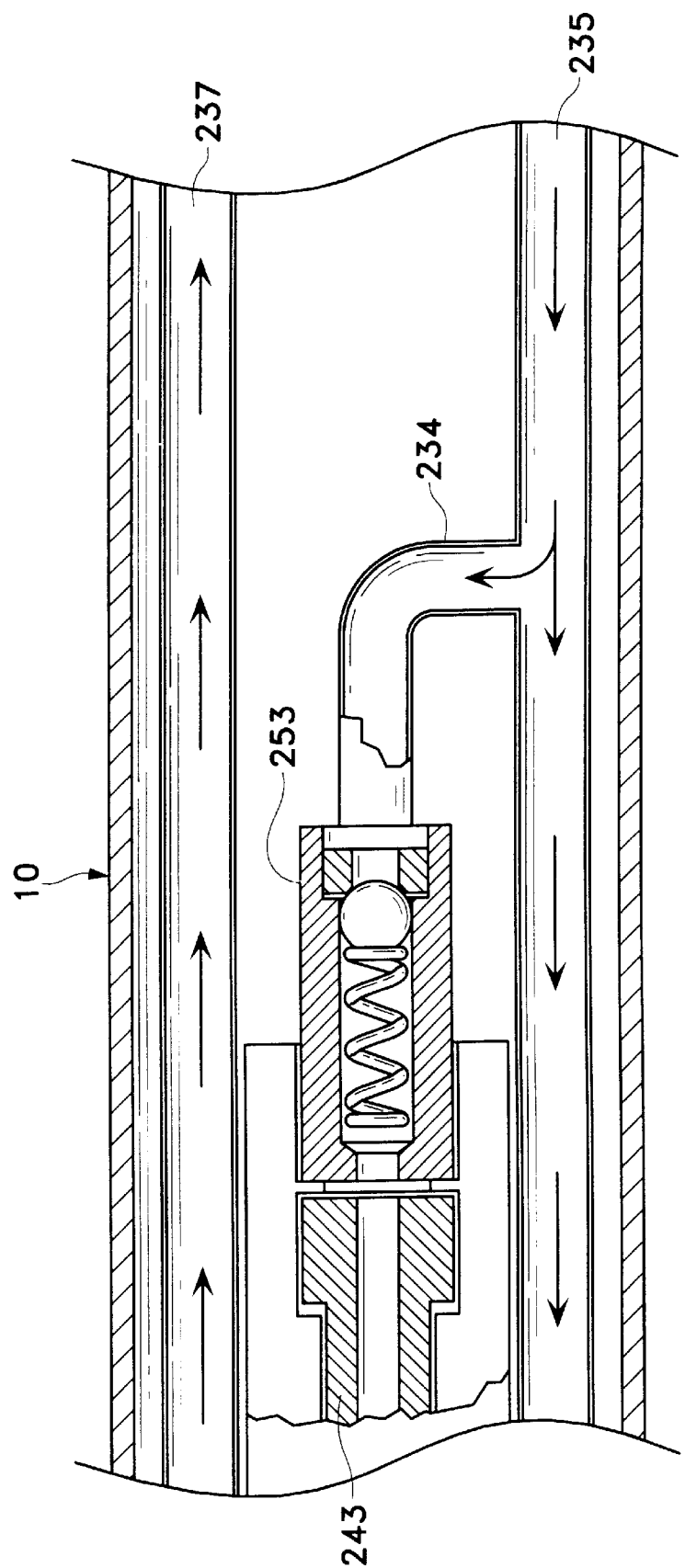
FIG. 9 is an exploded, partial cross-section view of one embodiment of the handpiece of the present invention.

As best seen in FIGS. 3, 4 and 7, surgical fluid may be supplied to pumping chamber 43 through lumen 34 or, as seen in FIG. 9, surgical fluid may be supplied to pumping chamber 243 through irrigation fluid lumen 234 which branches off main irrigation lumen 235 supplying cool surgical fluid to the operative site. As seen in FIG. 9, aspiration lumen 237 may be contained internally to handpiece 10. The numbers in FIG. 9 are identical to the numbers in FIG. 7 except for the addition of "200" in FIG. 9.

Any of a number of methods can be employed to order limit the amount of heat introduced into the eye. For example, the pulse train duty cycle of the heated solution can be varied so that the total amount of heated solution introduced into the eye does not vary with the pulse frequency. Alternatively, the aspiration flow rate can be varied as a function of pulse frequency so that as pulse frequency increases aspiration flow rate increases proportionally.

This description is given for purposes of illustration and explanation. It will be apparent to those skilled in the relevant art that changes and modification may be made to the invention described above without departing from its scope or spirit. For example, it will be recognized by those skilled in the art that the present invention may be combined with ultrasonic and/or rotating cutting tips to enhance performance.

We claim:

1. A method of liquefying a lens, comprising the steps of:
   a) providing a handpiece having a first lumen and a pumping chamber attached to the first lumen, the pumping chamber being formed by a pair of electrodes across which electrical current will flow;

b) supplying a surgical fluid to the pumping chamber through the first lumen;

c) delivering electrical current to the across the pair of electrodes so as to boil the surgical fluid contained within the pumping chamber, whereby the gas formed by the boiling surgical fluid expands out of the pumping chamber through a second lumen but is prevented from expanding out of the pumping chamber through the first lumen; and d) allowing the boiled surgical fluid to be propelled down and out of the second lumen so as to contact the liquefy a lens.

2. The method of claim 1 wherein the pumping chamber produces pressure pulses with a force of between 0.03 grams and 3.0 grams.

3. The method of claim 1 wherein the pumping chamber produces pressure pulses with a rise time of between 1 gram/second and 3,000 grams/second.

4. A method of liquefying a lens, comprising the steps of:

a) providing a handpiece having a first lumen and pumping chamber attached to the first lumen, the pumping chamber being formed by a pair of electrodes across which electrical current will flow, the pumping chamber producing pressure pulses with a force of between 0.03 grams and 3.0 grams and a rise time of between 1 gram/second and 3,000 grams/second;

b) supplying a surgical fluid to the pumping chamber through the first lumen;

c) delivering electrical current to and across the pair of electrodes so as to boil the surgical fluid contained within the pumping chamber, whereby the gas formed by the boiling surgical fluid expands out of the pumping chamber through a second lumen but is prevented from expanding out of the pumping chamber through the first lumen, and d) allowing the boiled surgical fluid to be propelled down and out of the second lumen so as to contact and liquefy a lens.

* * * * *